United States Patent [19]
Reid et al.

[11] Patent Number: 5,403,868
[45] Date of Patent: Apr. 4, 1995

[54] CAPSAICIN DERIVATIVES

[75] Inventors: Derek J. Reid; Christopher S. J. Walpole, both of London; Roger Wrigglesworth, Kemsing, all of Great Britain

[73] Assignee: Sandoz Ltd., Basle, Switzerland

[21] Appl. No.: 195,432

[22] Filed: Feb. 14, 1994

Related U.S. Application Data

[63] Continuation of Ser. No. 15,685, Feb. 9, 1993, abandoned, which is a continuation of Ser. No. 683,928, Apr. 11, 1991, abandoned, which is a continuation of Ser. No. 455,655, Dec. 21, 1989, abandoned.

[30] Foreign Application Priority Data

Dec. 23, 1988 [GB] United Kingdom ............... 8830143
Oct. 5, 1989 [GB] United Kingdom ............... 8922440

[51] Int. Cl.⁶ ................... A61K 31/17; C07C 335/12
[52] U.S. Cl. ............................... 514/586; 564/27
[58] Field of Search ................ 564/27, 26, 28, 29; 514/586, 585, 587

[56] References Cited

U.S. PATENT DOCUMENTS

| | | | |
|---|---|---|---|
| 3,852,347 | 12/1974 | Krapcho | 564/53 |
| 4,460,602 | 7/1984 | Buckwalter et al. | 564/26 |
| 5,045,565 | 9/1991 | Gardner et al. | 514/487 |
| 5,099,030 | 3/1992 | Gardner et al. | 548/478 |

FOREIGN PATENT DOCUMENTS

| | | |
|---|---|---|
| 68590 | 1/1983 | European Pat. Off. . |
| 149544 | 7/1985 | European Pat. Off. . |
| 226223 | 6/1987 | European Pat. Off. . |
| 282127 | 9/1988 | European Pat. Off. . |
| 347000 | 12/1989 | European Pat. Off. . |
| 401903 | 12/1990 | European Pat. Off. . |
| 2168975 | 7/1986 | United Kingdom . |
| 2206347 | 1/1989 | United Kingdom . |

*Primary Examiner*—Glennon H. Hollrah
*Assistant Examiner*—Scott C. Rand
*Attorney, Agent, or Firm*—Robert S. Honor; Melvyn M. Kassenoff; Joseph J. Borovian

[57] ABSTRACT

Novel capsaicin derivatives of general formula I

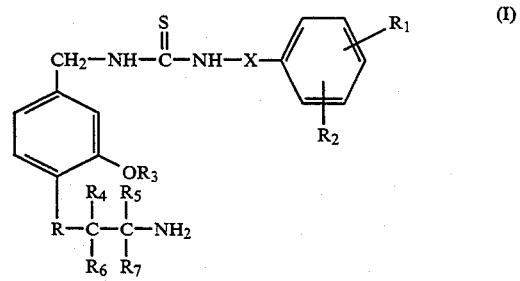

wherein R, $R_1$ to $R_7$ and X may be a variety of substituents, processes for the production thereof, pharmaceutical compositions containing them and use thereof as pharmaceuticals.

6 Claims, No Drawings

CAPSAICIN DERIVATIVES

This is a continuation of application Ser. No. 08/015,685, filed Feb. 9, 1993, now abandoned, which in turn is a continuation of application Ser. No. 07/683,928, filed Apr. 11, 1991, now abandoned, which in turn is a continuation of application Ser. No. 07/455,655, filed Dec. 21, 1989, now abandoned.

The present invention relates to novel compounds having pharmaceutical properties, to processes for their production, pharmaceutical compositions comprising them and their use as pharmaceuticals.

The present invention provides in one aspect compounds of formula I

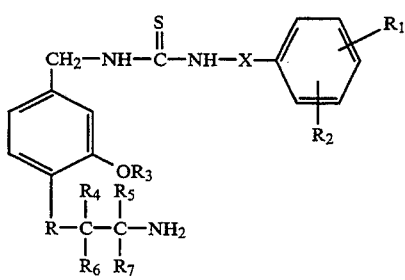

wherein:
$R_1$ is halogen, $C_{1-4}$alkyl, phenyl, benzyl, substituted or unsubstituted benzyloxy, nitro, cyano, trifluoromethyl, formylamino or $C_{1-16}$alkoxy, $R_2$ is hydrogen or has any one of the meanings given for $R_1$, $R_3$ is hydrogen or $C_{1-4}$alkyl, $R_4$ and $R_5$, independently, are hydrogen, halogen, $C_{1-5}$alkyl, substituted $C_{1-5}$alkyl, substituted or unsubstituted aryl, COOH, COOR$_8$ or CONR$_9$R$_{10}$ wherein $R_8$ is $C_{1-5}$alkyl, and each of $R_9$ and $R_{10}$ independently is hydrogen or $C_{1-5}$alkyl, $R_6$ and $R_7$, independently have the meanings given for $R_4$ and $R_5$ or, together with the carbon atoms to which they are attached form a substituted or unsubstituted $C_{3-7}$cycloalkyl group, $R$ is O, S or NH and $X$ is $-(CH_2)_n-$ or $-(CH_2)_m-CH=CH-(CH_2)_r-$ wherein $n$ is 1, 2 or 3 and each of $m$ and $r$ is independently zero or an integer of from 1 to 3, and physiologically hydrolyzable and acceptable esters or amides and pharmaceutically acceptable salts thereof.

The compounds of formula I wherein X is $-(CH_2)_m-CH=CH-(CH_2)_r-$ may exist in both cis or trans isomeric forms, i.e. as Z and E isomers. The present invention is to be understood as embracing both the individual cis and trans isomers as well as mixtures thereof.

Substituted benzyloxy groups as $R_1$ include benzyloxy substituted by halogen or phenyl. Substitutions may be, e.g. at the 2- and/or the 4-position of the benzyloxy group. Suitably the benzyloxy group is monosubstituted. Preferably the benzyloxy group is monosubstituted at the 4-position.

Alkyl groups as $R_1$ through $R_{10}$ as well as the alkyl moiety of alkoxy groups as $R_1$ or $R_2$ may be branched or straight chain. Preferably such alkyl groups and moieties are straight chain.

By halogen is meant fluorine, chlorine, bromine or iodine.

Preferred aryl groups as $R_4$ to $R_7$ are phenyl or naphthyl. Such groups may be unsubstituted or substituted, e.g. mono-, di- or tri-substituted phenyl or naphthyl. Preferred substituents are selected from halogen, hydroxy, amino and carboxy. Especially preferred aryl groups as $R_4$ to $R_7$ are phenyl or substituted phenyl.

A group of compounds of formula I comprises those compounds in which $R_1$ is as defined above but excluding substituted benzyloxy and R, $R_2$ to $R_{10}$ and X are as defined above.

In the compounds of formula I, the following significances are preferred either individually or in any combination or sub-combination:

1. $R_1$ is halogen, $C_{1-4}$alkyl, $C_{1-6}$alkoxy or substituted or unsubstituted benzyloxy, especially halogen, $C_{1-6}$alkoxy or substituted or unsubstituted benzyloxy. When $R_1$ is $C_{1-16}$alkoxy, this is suitably n-octyloxy. When $R_1$ is substituted benzyloxy, this is suitably halo- or phenyl-benzyloxy, especially 4-halo- or 4-phenyl-benzyloxy. $R_1$ is preferably in the 4-position.

2. $R_2$ is hydrogen, halogen or $C_{1-4}$alkyl, especially hydrogen or halogen. When $R_2$ is other than hydrogen, it is preferably in the 2-position.

3. $R_3$ is hydrogen or methyl, suitably methyl.

4. $R_4$ to $R_7$, independently are hydrogen, methyl, ethyl, $C_{1-5}$alkyl substituted by OH or NH$_2$, phenyl or $C_{1-5}$alkyl-phenyl. More preferably, at least one of $R_4$ to $R_6$ is hydrogen. Yet more preferably, at least three of $R_4$ to $R_7$, e.g. $R_4$, $R_5$ and $R_6$ are hydrogen. Most preferably, all of $R_4$ to $R_7$ are hydrogen.

5. R is $-O-$.

6. X is $-(CH_2)_n-$, wherein n has the meanings given above. Preferably n is 1 or 2, especially 2.

7. X is $-(CH_2)_m-CH=CH-(CH_2)_r-$ in which one of m and r is zero and the other is 1. More preferably, both m and r are zero. Most preferably, such groups X are in Z isomeric form.

An especially preferred group of compounds of formula I are those wherein X has the meanings given under 6 above and especially such compounds wherein $R_1$ and $R_2$ are as defined under 1 and 2 above. A further preferred group of compounds of formula I are those wherein X has the meanings given under 6 above and each of $R_4$ to $R_7$ is hydrogen, especially such compounds wherein $R_1$ and $R_2$ are as defined under 1 and 2 above.

By the term "physiologically-hydrolyzable and -acceptable esters or amides" as used herein is meant esters (e.g. compounds of formula I wherein one or more of $R_4$ to $R_7$ is $-COOH$ and/or $R_3$ is hydrogen) or amides which are hydrolyzable under physiological conditions to produce acids or alcohols which are themselves nontoxic, i.e. have no significant undesirable side effects at desired dosage levels. Such esters include esters with mono- and di-carboxylic acids, e.g. esters of the compounds of formula I in which the 3-hydroxy group is acetylated and esters with lower, e.g. $C_{1-4}$ alkanols. Such amides include those derived from organic carboxylic acids e.g. acetic acid amides including amino acids e.g. glycine amides.

The present invention also provides a process for the production of the compounds, amides, esters and salts of the invention which process comprises:

a) for the production of a compound of formula I, reacting a compound of formula II

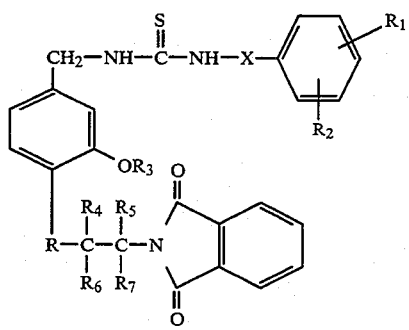

(II)

wherein R, $R_1$ to $R_7$ and X are as defined above,
with hydrazine b) for the production of a compound of formula I, removing at least one amino protecting group which is present in an amino protected compound of formula I, c) for the production of a physiologically-hydrolyzable and -acceptable ester or amide of a compound of formula I, esterifying or amidating a compound of formula I, for example in which $R_3$ is hydrogen, by reaction with an appropriate acylating or amidating agent, respectively, d) for the production of a compound of formula I wherein X is $-(CH_2)_m-CH=CH-(CH_2)_r-$ in Z-isomeric form, isomerizing a compound of formula I wherein X is $-(CH_2)_m-CH=CH-(CH_2)_r-$ in E-isomeric form and recovering a compound of formula I thus obtained in free or salt form.

Process step a) may be carried in analogy with known methods, for example by reaction of the compound of formula II with hydrazine hydrate in an inert solvent or diluent, e.g. alkane/alkanol, at ambient or elevated temperatures, e.g. at a temperature of from 0° C. to reflux. Process step b) may be carried out in accordance with standard techniques for the removal of amino protecting groups as known in the art. Suitable amino protecting groups include p-toluene sulphonyl, benzyl, formyl and trifluoroacetyl.

Process step c) may also be performed employing conventional acylation or amidation methods e.g. by reaction with an appropriate e.g. $C_{1-4}$ acyl halide or anhydride.

The trans isomers of compounds of formula I wherein X is $-(CH_2)_m-CH=CH-(CH_2)_r-$ may be converted into the cis (Z) isomers in conventional manner, e.g. by irradiation. Individual cis and trans isomers may be obtained in accordance with techniques known in the art, e.g. separation of cis/trans isomer mixtures, for example by chromatography.

Compounds of formula II used as starting materials in process step (a) may be produced by either of the following Reaction schemes, A or B

REACTION SCHEME A

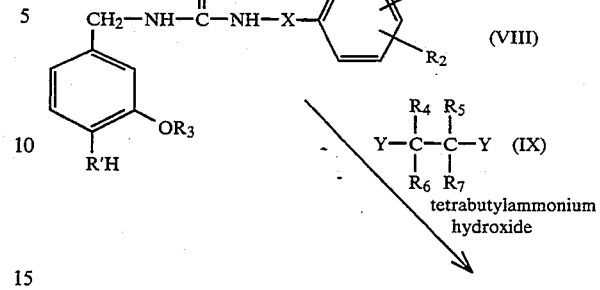

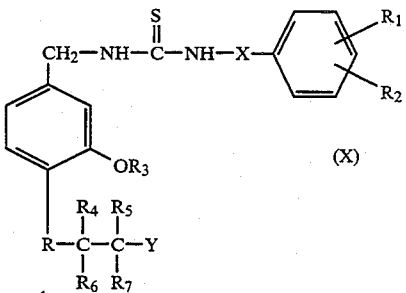

wherein R, $R_1$ to $R_7$ and X are as defined above, Y is halogen, e.g. bromine and R' is O or S.

Compounds of formula VIII, in which R is O, are described, along with processes for their production in, for example, published GB patent application 2,206,347A. Other compounds of formula VIII may be produced in similar or analogous fashion to the known compounds.

In Reaction Scheme B, on the following page, R, $R_1$ to $R_7$ and X are as defined above and Y is halogen, e.g. bromine.

The intermediates in Reaction Schemes A and B of formulae X, VIII, VI, V, II and III are new and also form part of the present invention per se.

REACTION SCHEME B

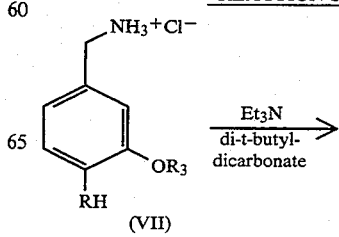

-continued
REACTION SCHEME B

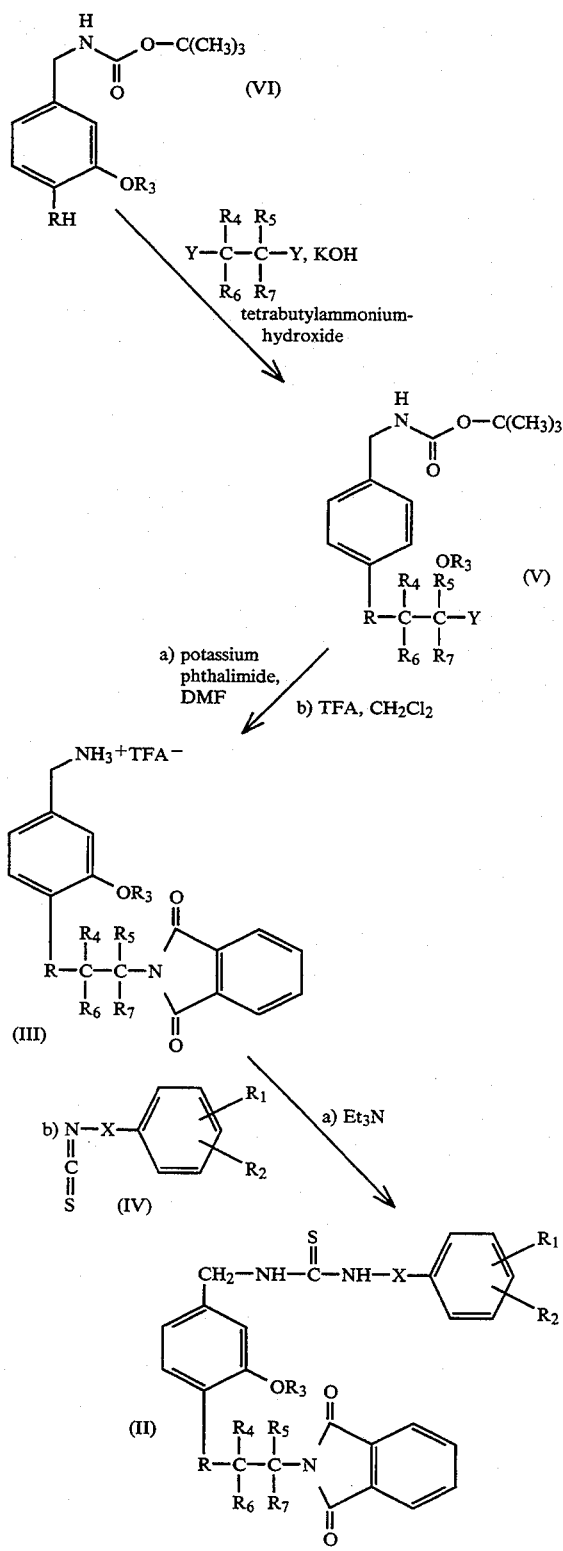

a) potassium phthalimide, DMF
b) TFA, CH₂Cl₂
a) Et₃N
b) (IV)

Insofar as the production of the starting materials is not particularly described, the compounds may be prepared by analogy with known methods.

The compounds of formula I as defined above may exist in free or salt form. Suitable pharmaceutically acceptable salts of compounds of formula I, e.g. wherein one or more of $R_4$ to $R_7$ is —COOH for use in accordance with the present invention include for example the sodium, potassium and calcium salts as well as quaternary ammonium, e.g. triethylammonium salts. Such salts also include pharmaceutically acceptable acid addition salts, e.g. salts with inorganic or organic acids such as hydrochloric acid, acetic acid, fumaric acid, citric acid and benzoic acid.

The following Examples are illustrative of the process of the present invention.

The following abbreviations are used:
DMF = dimethylformamide
TLC = thin layer chromatography

EXAMPLE 1

N-[4-(2-Aminoethoxy)-3-Methoxy-Benzyl)]-N'-[2-(4-Chlorophenyl)-Ethyl)]Thiourea 2.0 g N-[4-(2-Phthalimidoethoxy)-3-methoxybenzyl]-N'-[2-(4-chlorophenyl)ethyl]thiourea (0.0038 mole) is suspended in 10 ml ethanol in a round bottomed flask and heated to 60° C. until the solution becomes homogeneous. 0.10 ml 1-Hexene and 0.95 ml of a 64% aqueous solution of hydrazine hydrate is added and the mixture heated for 90 minutes. After 15 minutes a white precipitate begins to form and a small amount of ethanol is added to keep the mixture mobile. The reaction is cooled, transferred to a separating funnel and 10 ml methyl-butyl ether, 5 ml water, 5 ml 1N NaOH and 0.5 ml 50% NaOH are added. The resulting mixture is shaken thoroughly and the organic layer extracted twice as above, then washed with brine. The organic layer is dried over $Na_2SO_4$, filtered and the solvent removed by evaporation. The residue is purified via flash column chromatography, eluting first with $CH_2Cl_2$: MeOH (10:1) and then with MeOH. The product fractions are evaporated and dried in vacuo (30° C., 0.1 mm Hg) to give the title compound as a solid colorless glass. The following compounds of formula I may be obtained analogously:

| Example | R | $R_1$ | $R_2$ | $R_3$ | $R_4$ to $R_7$ | X |
|---|---|---|---|---|---|---|
| 2 | O | 4-F | H | $CH_3$ | H | $(CH_2)_2$ |
| 3 | O | 4-Cl | 2-Cl | $CH_3$ | H | $(CH_2)_2$ | and also the following compounds of formula I

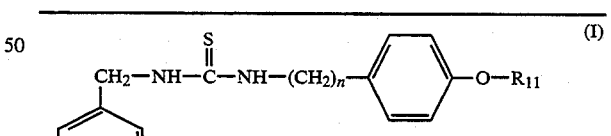

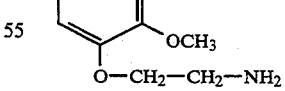

| EXAMPLE | $R_{11}$ | n |
|---|---|---|
| 4 | benzyl | 2 |
| 5 | 4-bromobenzyl | 2 |
| 6 | n-octyl | 2 |
| 7 | n-octyl | 1 |
| 8 | 4-chlorobenzyl | 2 |
| 9 | 4-phenylbenzyl | 2 |

CHARACTERIZING DATA

1. ¹H NMR data [400 MHz]

Example 1: [D₆DMSO] δ2.80(2H, t,J=7.2 Hz), 2.99(2H,t,J=5.5 HZ), 3.61(2H,S,broad), 3.75(3H,s), 4.00(2H,t,J=5.5 Hz), 5.57(2H,s,broad), 6.79(1H ,d,J=1.8 Hz), 6.94(1H,d,J=8.1 Hz), 6.96(1H,d,J=1.6 Hz), 7.26(2H ,d,J=8.2 Hz), 7.34(2H,d,J=8.1 Hz), 7.75(1H,s,broad), 7.99(1H ,s,broad)

Example 2: [CDCl₃] δ1.55(3H,s,broad), 2.84(2H,t,J=6.9 Hz), 3.10(2H,t,J=5.3 Hz), 3.74(2H,s,broad), 3.83(3H,s), 4.02(2H, t,J=5.3 Hz), 4.41(2H,s,broad), 5.72(1H,s,broad), 6.18(1H,s,broad), 6.70–6.81(2H,m), 6.93–6.98(2H,m), 7.06–7.10(2H,m)

Example 3: [CDCl₃] δ1.52(3H,s,broad), 2.99(2H, t,H=7.0 Hz), 3.11(2H, t,J=5.3 Hz), 3.75(2H,s,broad), 3.84(3H,s), 4.03(2H, t,J=5.3 Hz), 4.45(2H,s,broad), 5.82(1H,s,broad), 6.17(1H,s,broad), 6.79–6.84(4H,m), 7.10–7.17(3H,m), 7.35(2H,d,J=1.8 Hz)

Example 4: [CD₃OD] δ2.80(2H,t,J=7.1 Hz), 3.09(2H,t,J=5.1 Hz), 3.68(2H,s,broad), 3.83(3H,s), 4.06(2H, t,J=5.1 Hz), 4.60(2H,s,broad), 5.04(2H,s), 6.80–7.13(5H,m), 7.29–7.43(4H,m)

Example 5: [CD₃D] δ2.78(2H,t,J=7.15 Hz), .13(2H,t,J=5.1 Hz), 3.68(2H,s,broad), 3.84(3H,s), 4.08(2H,t,J=5.1 Hz), 4.60(2H,s,broad), 5.01(2H,s), 6.81–7.12(7H,m), 7.43(4H,dd,J=8.3 Hz,J=64.5 Hz)

Example 6: [CD₃OD] δ0.92(3H,m), 1.28–1.38(8H,m), 1.46(2H,m), 1.75(2H,m), 3.27(2H, t,J=5.0 Hz), 3.83(3H,s), 3.94(2H, t,J=6.4 Hz), 4.16(2H, t,J=5.0 Hz), 4.63(4H,s,broad), 6.82–7.90(5H,m), 7.19–7.21(2H,m)

Example 7: [CD₃OD] δ0.90(3H,m), 1.28–1.35(8H,m), 1.46(2H,m), 1.74(2H,m), 2.79(2H, t,J=7.25 Hz), 3.16(2H,t,J=5.15 Hz), 3.68(2H,s,broad), 3.85(3H,s), 3.92(2H,t,J=6.45 Hz), 4.11(2H,t,J=5.15 Hz), 4.63(2H,s,broad), 6.70–7.11(7H,m)

Example 8: [CD₃OD] δ2.8(2H,t,J=7.15 Hz), 3.02(2H,t,J=5.25 Hz), 3.68(2H,s,broad), 3.83(3H,s), 4.03(2H,t,J=5.25 Hz), 4.59(2H,s,broad), 5.03(2H,s), 6.80–6.97(5H,m), 7.11(2H,d,J=8.45 Hz), 7.38(4H,dd,J=8.5 Hz,J=13.4 Hz)

Example 9: [d₆DMSO] δ2.74(2H,t,J=7.3 Hz), 2.94(2H,t,J=5.65 Hz), 3.56(2H,s,broad), 3.74(3H,s), 3.95(2H,t,J=5.65 Hz), 4.56(2H,s,broad), 5.12(2H,s), 6.78(1H,m), 6.80–6.97(4H,m), 7.15(2H,d,J=8.5 Hz), 7.37(1H,m), 7.45–7.54(5H,m), 7.66–7.69(4H,m)

The compound of Example 9 has a melting point of 90°–92° C.

HPLC Retention time

The retention times of the compounds of Examples 1 to 9 were measured on a C-18 Microbondapak ® reverse phase column using the following gradient and conditions:

Solution A: 0.1% trifluoroacetic acid
Solution B: acetonitrile

| TIME (min) | FLOW RATE (ml/min) | % A | % B |
|---|---|---|---|
| 0 | 2.25 | 90 | 10 |
| 2 | 2.25 | 90 | 10 |
| 6 | 2.25 | 45 | 55 |
| 22 | 2.25 | 40 | 60 |
| 29 | 2.25 | 0 | 100 |
| 31 | 2.25 | 90 | 10 |

The following results were obtained:

| EXAMPLE | RETENTION TIME (min) |
|---|---|
| 1 | 9.404 |
| 2 | 9.415 |
| 3 | 9.740 |
| 4 | 9.752 |
| 5 | 10.297 |
| 6 | 10.827 |
| 7 | 11.317 |
| 8 | 10.080 |
| 9 | 10.482 |

Following the steps of Reaction Scheme B the compounds used as starting materials may be prepared as follows:

a) t-Boc-vanillylamine 18.0 g Vanillylamine hydrochloride (0.095 mole) and 10.6 g triethylamine (0.11 mole) are dissolved in 250 ml water and placed in a 1 L round bottomed flask. 20.5 g di-tert-butyldicarbonate (0.095 mole) in 200 ml dioxan is added with stirring, over a period of 15 minutes. The resulting mixture is stirred overnight at room temperature.

The dioxan is removed in vacuo and the aqueous residue extracted with CHCl₃ (5×10 ml). The combined extracts are dried over MgSO₄, filtered and the solvent removed in vacuo to leave a brown oil which is purified via flash column chromatography (cyclohexane: EtOAc/5:2) to give a colorless oil which crystallizes on standing. [t.l.c. cyclohexane: EtOAc/1:1; r.f.=0.5]

b) t-Boc-(4-(2-bromoethoxy)-3-methoxybenzylamine 21.0 g t-Boc-vanillylamine (0.083 mole), 250 ml 1,2.dibromoethane, 66 ml 40% KOH and 6.6 ml 40% tetrabutylammonium hydroxide are combined in a 500 ml round bottomed flask and the resulting mixture is heated at 50° C. for 3 hours with rapid stirring.

The mixture is cooled, diluted with 200 ml CH₂Cl₂, washed with water (3×200 ml) and the combined aqueous washings extracted once with 600 ml CH₂Cl₂. The combined organic layers are washed with brine, dried over MgSO₄, filtered and the solvent removed in vacuo to leave a white solid which is used without further purification. [t.l.c. cyclohexane: EtOAc/1:1; r.f.=0.6]

c) t-Boc-(4-(2-phthalimidoethoxy)-3-methoxybenzylamine 23.0 g t-Boc-(4-(2-bromoethoxy)-3-methoxybenzylamine (0.064 mole) and 11.8 g potassium phthalimide (0.064 mole) are suspended in 500 ml dry DMF in a round bottomed flask. The resulting suspension is heated at 50° C. for 2 hours with rapid stirring. After 30 mins of this heating/stirring, the mixture becomes homogeneous. The mixture is then cooled and the DMF removed under high vacuum. The resulting solid residue is purified via flash column chromatography (cyclohexane: EtOAc/1:1) to give a white solid. [t.l.c. (cyclohexane: EtOAc/1:1) rf=0.45.

d) 4-(2-phthalimidoethoxy)3-methoxybenzlamine.TFA 26.5 g t-Boc-(4-(2-phthalimidoethoxy)-3-methoxybenzylamine (0.062 mole) is dissolved in 200 ml CH₂Cl₂ in a 500 ml round bottomed flask. 15 ml trifluoroacetic acid is added dropwise with stirring. On completion of the addition, the mixture is stirred for a further 2 hours at room temperature (the reaction is shown to be completed by the loss of staring material (cyclohexane: EtOAc/1:1)). The solvent is removed in vacuo, initially on the water pump and then high vacuum. The resulting colorless oil solidifies on standing and is used without further purification.

e) N-[4-(2-phthalimidoethoxy)-3-methoxybenzyl]-N-[2-(4-chlorophenyl)ethyl]thiourea 2.0 g 4-(2-phthalimidoethoxy)-3-methoxybenzylamine.TFA (0.005 mole) and 0.5 g Et$_3$N (0.005 mole) are suspended in 30 ml dry EtOAc under an atmosphere of dry nitrogen. 0.9 g 2-(4-chlorophenyl)ethylisothiocyanate (0.0045 mole) in dry 10 ml EtOAc is added dropwise and the mixture stirred at room temperature for 3 hours.

The EtOAc is removed in vacuo, the residue suspended in 50 ml water and then extracted with 3×50 ml CH$_2$Cl$_2$. The combined organic layers are dried over MgSO$_4$, filtered and the solvent removed in vacuo to leave a brown oil which is purified via column chromatography [tlc (cyclohexane: EtOAc/1:1) rf=0.2]. Melting point=59°-61° C.

The compounds and amides and esters of the invention have pharmaceutical, in particular analgesic and anti-inflammatory, utility as may be shown in standard test models, for example as follows:

1. TAIL-FLICK TEST IN THE MOUSE

The method is based on that of D'Amour et al. J. Pharmacol. Exp. Ther. 72, 74–79 (1941), but employing unstarved mice (o+o, 16-25 g). Animals are divided into control and test groups, control animals receiving a vehicle injection only. Each test animal is placed in an individual perspex cylinder to prevent movement with its tail protruding along a narrow groove. The tail of each animal is exposed to a beam of radiant heat at ca. 35 mm from the tail root, from a lamp of known output and temperature, placed directly under the tail. Test substance is administered p.o. or s.c. 30 mins. post introduction into the cylinder. The time in seconds taken by the mouse to flick its tail out of the light beam is recorded 30 to 15 mins prior to administration of test substance. Animals whose reaction times differ by more than 25 % are discarded. Reaction time is re-determined 15 and 30 mins post administration. Extension of reaction time by >75 % over mean pre-treatment values in the same animal are taken as indicative of analgesic response. Three doses are employed per test substance and 10 animals per dose. ED$_{50}$ values (95 % confidence limits) are estimated in accordance with the method of Litchfield and Wilcoxon and represent the dose prolonging treatment reaction time by >75 % in 50 % of test animals.

Compounds and amides and esters of the invention are active in the above test model at dosages of the order of from about 1.0 to about 120.0 μm/kg, s.c.

2. YEAST INDUCED INFLAMMATION TEST IN THE MOUSE

20 μl, 20 % fresh yeast suspension is injected into the plantar region of one hind paw and saline is injected into the other. Degree of inflammation is estimated by the relative increase in paw weight (yeast injected v.s.saline) 2 hrs. post-injection. Test substance is administered s.c. at varying dosage at the same time as yeast/saline treatment. 5 animals are used/dose and testing at each dose is repeated 2-3 times, control and test values being compared statistically as above. ED$_{50}$ values are taken as the dosage required to effect 50 % inhibition of inflammation as compared with control animals not receiving test substance, and are established from dose response curves plotting % inflammation vs. dose. Compounds and esters of the invention are active in the above test model at dosages of the order of from about 2.5 to 100 μM/kg, s.c.

The compounds, esters, amides and pharmaceutically acceptable salts of the invention are accordingly useful as pharmaceuticals, e.g. as analgesics for the treatment of pain of various genesis or aetiology, for example dental pain and headache, particularly vascular headache, such as migraine, cluster, and mixed vascular syndromes as well as nonvascular, tension headache, and as anti-inflammatory agents for the treatment of inflammatory diseases or conditions, for example the treatment of arthritis and rheumatic diseases, Raynaud's disease, inflammatory bowel disorders, trigeminal or herpetic neuralgia, inflammatory eye disorders e.g. uveitis, psoriasis, cystitis as well as other chronic inflammatory conditions.

Having regard to their analgesic/anti-inflammatory profile they are, in particular, useful for the treatment of inflammatory pain, for the treatment of hyperalgesia and, in particular, the treatment of severe chronic pain, e.g. for the treatment of deafferentation pain as an alternative to surgical procedures.

According to a further embodiment, the compounds of formula I, their esters, amides and pharmaceutically acceptable salts are also useful for the prophylactic or curative treatment of epithelial tissue damages or dysfunction, e.g. spontaneous lesions, and for the control of disturbances of visceral motility at respiratory, genitourinary, gastrointestinal and vascular level, e.g. for treating wounds, burns, skin allergic reactions, pruritus and vitiligo, for the prophylactic or curative treatment of gastrointestinal disorders such as gastric ulceration, duodenal ulcers and diarrhea, for the prophylactic or curative treatment of gastric lesions induced by necrotizing agents, for example ethanol, for the treatment of vasomotor or allergic rhinitis and for the treatment of bronchial disorders or bladder disorders. The utility in treating as epithelial tissue damages or dysfunction may be shown in standard test models, for example as follows:

ETHANOL-INDUCED GASTRIC LESIONS

The tests are carried out employing male rats (200–250 g) fasted overnight but with free access to water. The test substance is administered s.c. or orally by a metal stomach tube. Absolute ethanol is given orally 30 min after the administration of the test substance and the animals are killed 1 hour later. The stomach is cut open along the greater curvature and pinned flat. Hemorrhagic erosions are quantified in two ways: area and length of the erosions.

On administration of a compound of formula I as test compound at a dosage of from ca. 0.1 to 20 mg/kg, substantial inhibition of the gastric lesions induced by ethanol is observed compared with results for control groups receiving placebo in lieu of the test compound.

For the above uses the required dosage will of course vary depending on the mode of administration, the particular condition to be treated and the effect desired. In general, however, satisfactory results are achieved at dosage rates of from about 1 to about 20 mg/kg, e.g. from about 1 to about 10 mg/kg, p.o. for analgesic use, and at dosage rates of from about 1 to about 20 mg/kg p.o. for anti-inflammatory use. Suitable daily dosage rates for larger mammals are thus of the order of from about 2 to about 1,000 or 2,000 mg p.o., e.g. from about 75 to 750 or 1,500 mg p.o. for analgesic use, and of the order of from about 10 to about 2,000 mg p.o. e.g. from about 75 to 1,500 mg p.o., for anti-inflammatory use, conveniently administered once, in divided dosages 2 to 4 times/day, or in sustained release or retard form.

Dosage forms suitable for oral administration accordingly comprise from about 0.5 to about 500 or 1,000 mg, e.g. from about 20 to about 375 or 750 mg (analgesic use) or from about 2.5 to about 1,000 mg, e.g. from about 20 to about 750 mg, (anti-inflammatory use) active ingredient (i.e. compound, ester, amide or pharmaceutically acceptable salt of the invention) admixed with an appropriate solid or liquid, pharmaceutically acceptable, diluent or carrier therefor.

In accordance with the foregoing the present invention also provides:

A.
i) for the treatment of pain of various genesis or aetiology, for example for the treatment of any such disease or conditions as hereinbefore set forth;
ii) for the treatment of inflammatory diseases and/or inflammatory pain, for example for the treatment of any such disease or conditions as hereinbefore set forth;
iii) for the prophylactic or curative treatment of epithelial tissue damage or dysfunction, gastrointestinal disorders or gastric lesions induced by necrotizing agents;
iv) for the control of disturbances of visceral motility at respiratory, genitourinary, gastrointestinal and vascular level; or
v) for the treatment of rhinitis and bronchial or bladder disorders, in a subject in need thereof, which method comprises administering to said subject an effective amount of a compound of formula I or a physiologically hydrolyzable and acceptable ester or amide thereof as hereinbefore defined, or a pharmaceutically acceptable salt thereof;

B. A compound of formula I or a physiologically-hydrolyzable and -acceptable ester or amide thereof as hereinbefore defined, or a pharmaceutically acceptable salt thereof, for use as a pharmaceutical, for example for use as an analgesic and/or anti-inflammatory agent and/or prophylactic or curative agent for the treatment of epithelial tissue damages or dysfunction; as well as C. A pharmaceutical composition comprising a compound of formula I or a physiologically-hydrolyzable and -acceptable ester or amide thereof as hereinbefore defined, or a pharmaceutically acceptable salt thereof, together with a pharmaceutically acceptable diluent or carrier therefor.

Suitable pharmaceutically acceptable salts of the compounds and esters of the invention include for example the sodium and potassium salts.

We claim:

1. A compound of formula I,

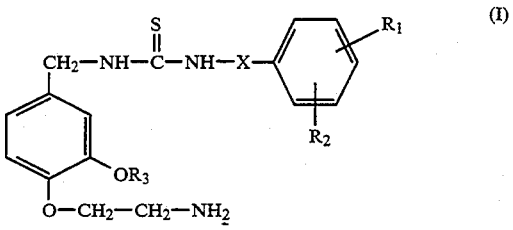

where
$R_1$ is halogen, $C_{1-4}$alkyl, $C_{1-16}$alkoxy or unsubstituted benzyloxy;
$R_2$ is hydrogen, halogen or $C_{1-4}$alkyl;
$R_3$ is hydrogen or $C_{1-4}$alkyl; and
X is $-(CH_2)-_n$, where n is 1, 2 or 3; or a pharmaceutically acceptable acid addition salt thereof.

2. A compound according to claim 1 wherein $R_1$ is halogen, $C_{1-16}$alkoxy or unsubstituted benzyloxy; $R_2$ is hydrogen or halogen; $R_3$ is hydrogen or methyl; and X is $-(CH_2)-_n$, where n is 1 or 2; or a pharmaceutically acceptable acid addition salt thereof.

3. A compound according to claim 1 selected from the group consisting of:
a) N-[4-(2-aminoethoxy)-3-methoxybenzyl]-N'-[2-(4-chlorophenyl)ethyl]thiourea,
b) N-[4-(2-aminoethoxy)-3-methoxybenzyl]-N'-[2-(4-fluorophenyl)ethyl]thiourea,
c) N-[4-(2-aminoethoxy)-3-methoxybenzyl]-N'-[2-(2,4-dichlorophenyl)ethyl]thiourea,
d) N-[4-(2-aminoethoxy)-3-methoxybenzyl]-N'-[2-(4-benzyloxyphenyl)ethyl]thiourea,
e) N-[4-(2-aminoethoxy)-3-methoxybenzyl]-N'-[2-(4-(n-octyloxy)phenyl)ethyl]thiourea, and
f) N-[4-(2-aminoethoxy)-3-methoxybenzyl]-N'-[4-n-octyloxybenzyl]thiourea;

or a pharmaceutically acceptable acid addition salt thereof.

4. A pharmaceutical composition comprising a pharmaceutically acceptable carrier or diluent and a therapeutically effective amount of a compound of claim 1 or a pharmaceutically acceptable acid addition salt thereof.

5. A method of treating pain, inflammation, gastrointestinal lesions induced by necrotizing agents, or vasomotor or allergic rhinitis, comprising administering to a subject in need of such treatment a therapeutically effective amount of a compound of claim 1 or a pharmaceutically acceptable addition salt thereof.

6. A method of treating pain comprising administering to a subject in need of such treatment a therapeutically effective amount of a compound of claim 1 or a pharmaceutically acceptable acid addition salt thereof.

* * * * *